United States Patent [19]

Taguchi

[11] Patent Number: 4,486,407

[45] Date of Patent: Dec. 4, 1984

[54] METHOD FOR ENHANCING PRODUCTION OF INTERFERON

[76] Inventor: Fumiaki Taguchi, No. 14-1, Yokodai 5-chome, Sagamihara-shi, Kanagawa, Japan

[21] Appl. No.: 470,740

[22] Filed: Feb. 28, 1983

[51] Int. Cl.³ .................... A61K 45/02; C12P 21/00
[52] U.S. Cl. ........................................ 424/85; 435/68
[58] Field of Search ................ 424/85, 315, 316, 317; 260/112 R, 112.5 R; 435/68

[56] References Cited

U.S. PATENT DOCUMENTS 3,773,924  11/1973  Ho et al. ............................... 424/85
3,929,991  12/1975  Steward et al. ....................... 424/85
4,266,024  5/1981  Swetly et al. .......................... 424/85

FOREIGN PATENT DOCUMENTS 102519  8/1980  Japan .

OTHER PUBLICATIONS

Cantell et al., Proc. of the Tissue Culture Association Workshop, Lake Placid, N.Y., pp. 35-38, 1973.
Chemical Abstracts, vol. 72, p. 14, Abst. No. 62742p, 1970.

*Primary Examiner*—Blondel Hazel
*Attorney, Agent, or Firm*—Sughrue, Mion, Zinn, Macpeak and Seas

[57] ABSTRACT

Interferon production, in vivo and in vitro, is enhanced by adding to the interferon production system, a chelating compound such as N-acetic acid derivatives of ammonia or polyamines. In one embodiment, a known interferon inducer is also utilized.

6 Claims, No Drawings

METHOD FOR ENHANCING PRODUCTION OF INTERFERON

BACKGROUND OF THE INVENTION

This invention relates to enhancement of production of interferon (hereinafter sometimes referred to as "IF") in living cells in vivo or in vitro. IF is produced in vivo by many animals, including humans, but only in extremely small amounts or quantities. Because of this, various IF production methods are currently being investigated which involve techniques such as recombinant DNA approaches to obtain cell lines capable of high levels of IF production, to lead to commercially viable IF manufacturing processes.

At one time, it was thought that IF only exhibited a prophylactic effect against viral infections. However, it has been proven that IF exhibits a therapeutic effect against viral diseases if administered in a sufficient amount (i.e., at high potency). Further, it has been recognized that IF exhibits antitumor acitivity, i.e., anticancer activity, against malignant tumors that are considered unrelated to viral infections. At the present time, IF is being considered as a present and potentially important therapeutic and prophylactic pharmaceutical, particularly in the prevention and treatment of various viral diseases and/or malignant tumors that have heretofore been difficult to prevent and treat. Thus, IF having the above-mentioned characteristics is extremely promising as a pharmaceutical for active or prophylatic treatment of viral diseases or malignant tumors without causing side effects.

IF is produced in vivo and can also be produced in vitro. In either case, enhancement of IF production would be of significant benefit. In other words, if the production of IF in vivo could be enhanced by any acceptable means, a method for preventing or treating viral diseases or tumors could result. Similarly, the enhanced production of IF in vitro would serve to provide higher yields of IF pharmaceuticals, i.e., preventing and treating agents for viral diseases or tumors.

SUMMARY OF THE INVENTION

Therefore, it is an object of the present invention to provide a method for increasing the production of interferon by living cells.

A further object of the present invention is to provide a method for enhancing the production of IF by mammals, including humans.

Another object of the present invention is to provide a method for active treatment in mammals, including humans, of viral diseases and/or tumors which respond to IF administration by enhancing the production of IF by said mammal.

Still another object of the present invention is to prevent in mammals the occurrence of viral diseases and/or tumors, the incidence of which is reduced by IF, by enhancing the production of IF by said mammal, particularly over a long period of time.

Other objects of the present invention will be apparent to the skilled artisan from the Detailed Description of the Invention, hereinbelow.

In accordance with the present invention, it has now been found that a chelating agent has an IF production-enhancement effect.

Accordingly, the method for enhancing the production of intereferon according to the present invention is characterized by adding an effective amount, that is an IF production enhancement amount, of a chelating agent to an interferon production system.

In a preferred embodiment for enhancing the production of interferon according to the present invention, a chelating compound and an interferon inducer are both added to an interferon production system.

Therefore, the present invention involves carrying out interferon production in the presence of an effective amount or under the influence of an effective amount of a chelating agent, in a preferred embodiment with joint administration of an IF inducer. The present invention is applicable to in vivo treatment or prophylaxis of diseases which respond to increased IF titers, as well as in vitro IF production methods which involve the production of IF by living cells and then collecting IF from the cells.

DETAILED DESCRIPTION OF THE INVENTION

Chelating Agent

The chelating compounds which can be used in the present invention are the well-known N-acetic acid derivatives of ammonia, ethylenediamine or polyethylenepolyamines (at least up to about the order of diethylenetriamine) or their non-toxic salts. The polyethylenepolyamine can contain up to about 2 ethylene units and up to about 3 amine moieties. Specific examples include nitrilotriacetic acid or its salts, ethylenediaminetetraacetic acid or its salts, diethylenetriaminepentaacetic acid or its salts, and the like. The salts may either be normal salts or acid salts (partially neutralized salts), and cations for the salts can include the ammonium ion, alkali metals (particularly, sodium), alkaline earth metals and the like. Sodium salts are the most general salts. Among them, typical compounds are ethylenediaminetetraacetic acid or its sodium salt, and diethylenetriaminepentaacetic acid or its sodium salt. These chelating compounds may be used as a mixture thereof.

Other types of chelating compounds can be used together with the above-disclosed types of chelating agent for increased effect, but at the present time it is not believed that these other chelating agents can be used alone to enhance IF production. These adjunct chelating agents which can be used together with the first group of the chelating compounds include biguanide, tetracycline, kanamycin, streptomycin, penicillin, cephalosporin, penicillamine, pleomycin, bacitracin, novobiocin, cycloserine, polymyxin and cycloheximide.

IF inducers are known in the art. In general, the IF inducers which can be used in the present invention include the various substances having an IF inducing property. At times, continuous administration of IF inducers is known to result in significantly lowered IF production after a period of higher IF production. One advantage of the present invention is to reduce this adverse IF inducer effect. As examples of IF inducers, there may be mentioned (1) viruses, such as Newcastle disease virus, Sendai virus and Influenza virus, (2) lipopolysaccharides derived from bacteria, such as a lipopolysaccharide extracted and purified from *Escherichia coli,* Salmonellae, Bifidobacterium, *Vibrio cholerae,* Lactobacillus, etc., (3) neutral or acid polysaccharides derived from bacteria, seaweeds, mushrooms, etc., such as an extract of Coriolus versicolor (Fr.) Quél (PSK) (as described in Gann, Vol. 69, pp. 223–228, (1978)), an extract of Shizophylum commune Fr. (SPG), and Lentinan (as described in *Cancer Res.*, Vol. 30, pp. 2776-2781, (1970)), (4) nucleic acids such as polyI:C (as described in *J. Gen. Physiol.*, Vol. 56, p. 905, (1970)), (5) cationic low polymers such as Tilorone (as described in *Science*, Vol. 169, p. 1214, (1970)), and (6) others, such as BCG, BCG-CWS (cell wall skeleton) (as described in *J. Natl. Cancer Inst.*, Vol. 52, pp. 95-101, (1974)), tuberculin, concanavalin A, protein A of Staphylococcus, OK-432 (as described in *Proc. 3rd Symp. on Drug Fukuoka, Metabo and Action*, pp. 112-137, (1971)), anaerobic Corynebacterium, Levamisol (as described in *Fogaty International Center Proceedings*, No. 28, N.I.H.: 3, (1977)), etc. Of these, typical examples are viruses and lipopolysaccharides derived from bacteria.

The enhancement of IF production according to the present invention is effected by adding the above-described chelating compound or mixture of chelating compounds alone or in combination with the above-described IF inducer to an in vivo or in vitro IF production system.

In detail, enhancement of in vivo IF production can be performed by administering the chelating compound or the chelating compound and the IF inducer to a host animal (human or other animals) orally or by injection. Enhancement of in vitro IF production comprises adding the chelating compound or the chelating compound and the IF inducer in the cultivation of human or other animals' cells, such as leukocyte, lymphocyte and lymphoblast (e.g., namalva cell) cells, etc.

In either case, administration or addition of the chelating compound and IF inducer may be performed several times. For obtaining a production system containing both of the chelating compound and the IF inducer, the time for administering or adding them to the IF production system may be staggered as long as the effect of using both is recognized.

The following examples are presented to illustrate the present invention, and are not intended to limit the scope of the invention in any manner.

Experimental Examples

Example 1

A lipopolysaccharide (LPS) of *E. coli* (250 μg/ml) alone or LPS (250 μg/ml) containing sodium ethylenediaminetetraacetate (EDTA) (10 mM) was administered to the tail vein of ICR-SPF male mice (body weight: 40±3 g; 4 mice per group) at a dose of 0.2 ml/mouse. Blood was taken after the time intervals as indicated in Table 1, and the IF activity in the serum in each mouse was determined with the average values for each group being set forth in Table 1.

The average results obtained are shown in Table 1.

The activity of the produced (induced) IF was assayed according to the 50% plaque reduction method (as described in William E. Stewart II, The Interferon System, (1979), Spinger-Verleg, Wien-N.Y., and R.R. Wagner, *Virology*, Vol. 13, pp. 323 (1961)) using *Vesicular stomatitis* virus, New Jersey strain (abbreviated as VSV) and L cells from mouse.

Example 2

Newcastle disease virus $B_1$ (NDV) (160 HAU/ml) alone or NDV (160 HAU/ml) containing EDTA (10 mM) was administered to ICR-SPF male mice (body weight: 40±3 g; 4 mice per group) through the tail vein at a dose of 0.2 ml/mouse. Blood was taken after the time intervals indicated in Table 2, and the IF activity in the serum in each group was determined as in Example 1.

The average results obtained are shown in Table 2.

Example 3

0.2 ml/mouse of EDTA (5 mM) alone, LPS (250 μg/ml) alone, or LPS (250 μg/ml) containing EDTA (5 mM) was intraperitoneally administered to ICR-SPF male mice (body weight: 30±3 g; 8 mice per group). After 4 days, each group was divided into two subgroups each consisting of 4 mice, and 0.2 ml/mouse of LPS (250 μg/ml) alone or LPS (250 μg/ml) containing EDTA (5 mM) was administered to each of the subgroups through the tail vein. Blood was taken after 3.5 hours, and the IF activity in the serum in each subgroup was assayed as in Example 1.

The average results obtained are shown in Table 3.

Example 4

EDTA (5 mM) alone, NDV (160 HAU/ml) alone or NDV (160 HAU/ml) containing EDTA (5 mM) was intraperitoneally administered to mice (body weight: 30±3 g; 8 mice per group) at a dose of 0.2 ml/mouse. After 4 days, each group was divided into two subgroups consisting of 4 mice/subgroup. To each of the subgroups was administered 0.2 ml/mouse of NDV (500 HAU/ml) alone or NDV (500 HAU/ml) containing EDTA (5 mM) through the tail vein. 7.5 hours thereafter, the blood was taken, and the IF activity in the serum of each subgroup was assayed as in Example 1.

The average results are shown in Table 4.

TABLE 1

| Blood Sampling Time (hour) | IF Activity in Serum | |
|---|---|---|
| | LPS Alone (units/ml) | LPS + EDTA (units/ml) |
| 1.5 | 850 | 850 |
| 2.5 | 1100 | 1100 |
| 3.5 | 250 | 950 |
| 4.5 | 100 | 1250 |
| 6.0 | 100 | 1000 |

TABLE 2

| Blood Sampling Time (hour) | IF Activity in Serum | |
|---|---|---|
| | NDV Alone (units/ml) | NDV + EDTA (units/ml) |
| 2 | 14000 | 16000 |
| 4 | 48000 | 150000 |
| 6 | 45000 | 180000 |
| 9 | 28000 | 90000 |
| 12 | 7200 | 130000 |

TABLE 3

| First Administration | IF Activity in Serum (after 2nd administration) | |
|---|---|---|
| | LPS Alone (units/ml) | LPS + EDTA (units/ml) |
| EDTA | 330 | 2100 |
| LPS | 90 | <50 |
| LPS + EDTA | 120 | 60 |

TABLE 4

| First Administration | IF Activity in Serum (after 2nd administration) | |
|---|---|---|
| | LPS Alone (units/ml) | LPS + EDTA (units/ml) |
| EDTA | 150000 | 720000 |
| NDV | 15000 | 7600 |
| NDV + EDTA | 50000 | 90000 |

Example 5

DTPA (sodium diethylenetriaminepentaacetate (5 mM)) alone or a phosphate-buffered saline (PBS) was intraperitoneally administered to ICR-SPF male mice (body weight: 30±3 g; 8 mice per group) at a dose of 0.5 ml/mouse. After 4 days, each group was divided into two subgroups each consisting of 4 mice, and 0.5 ml/mouse of DTPA (5 mM) was intraperitoneally administered to one subgroup of each group. After 30 minutes, all the mice received 0.2 ml/mouse of LPS (250 μg/ml) through the tail vein. Three hours and 6 hours after the LPS administration to all mice blood was taken and the IF activity in the serum in each subgroup was determined as in Example 1. The average results obtained are shown in Table 5.

TABLE 5

| First Administration | Second Administration | IF Activity in Serum | |
|---|---|---|---|
| | | 3 Hrs* (units/ml) | 6 Hrs* (units/ml) |
| PBS | LPS | 180 | <10 |
| PBS | DTPA + LPS | 150 | 70 |
| DTPA | LPS | 600 | 200 |
| DTPA | DTPA + LPS | 110 | 220 |

*The time elapsed from the second administration

Example 6

10 mM of EDTA was intraperitoneally administered to ICR-SPF male mice (body weight: 30±3 g; 4 mice per group) at a dose of 0.2 ml/mouse, and 4 days thereafter 0.2 ml/mouse of EDTA (5 mM) was again administered through the tail vein. Seven hours thereafter, the blood was taken, and the IF activity in the serum was assayed as in Example 1.

The average results obtained are shown in Table 6.

TABLE 6

| Serum | IF Activity in Serum (units/ml) |
|---|---|
| Normal mouse | <10 |
| Mouse having received EDTA once | <10 |
| Mouse having received EDTA twice | 700 |

Example 7

5 mM of DTPA or of phosphate-buffered saline (PBS) was intraperitoneally administered to ICR-SPF male mice (body weight: 30±3 g; 4 mice per group) at a level of 0.5 ml/mouse. Four days thereafter, as a second administration, 0.5 ml/mouse of DTPA (5 mM) or PBS was again intraperitoneally administered. Three hours and 6 hours after the second administration, the blood was taken, and the IF activity in the serum in each group was assayed as in Example 1.

The average results obtained are shown in Table 7.

TABLE 7

| First Administration | Second Administration | IF Activity in Serum | |
|---|---|---|---|
| | | 3 Hrs* (units/ml) | 6 Hrs* (units/ml) |
| PBS | PPS | <10 | <10 |
| PBS | DTPA | <10 | <10 |
| DTPA | PPS | <10 | <10 |
| DTPA | DTPA | 80 | 50 |

*The time elapsed after the second administration

As can be understood from the above examples, the chelating compounds used herein not only increase the rate of IF production, but also prolong an elevated rate of IF production for an extended period of time. Furthermore, the chealting agents of the present invention also appear to induce IF production, although at this time it is preferred to use the chelating agents with a conventional IF inducer. Through the present invention, it is possible to cause production of IF of high potency rapidly after administration of an IF inducer. As noted above, and as illustrated by certain of the examples hereinbefore, the present invention eliminates or reduces the low level of IF production occurring through repeated or continuous administration of an IF inducer.

It is not known at this time whether or not the cellular IF production process route is changed by the administration of the chelating agent. Alteration and/or acceleration and/or other phenomena may be involved.

With knowledge of the above-disclosed information, including the specific examples hereinbefore, the skilled artisan can readily determine through routine experimentation suitable dosages and dosage regimens for a particular IF in vivo or in vitro production system. Where active or prophylactic treatment of disease is involved, serum titers can be determined even on a daily basis if needed, with increasing time intervals between IF serum titer determinations as a history is developed for the particular combination of chelating agent, optional inducer, and host.

The chelating agents can be administered in combination with any suitable pharmaceutical carrier, whether liquid or solid, such as the various sterile aqueous-based carriers used for injectables.

Variations of the invention will be apparent to the skilled artisan. For example, the present invention can be used in IF production processes where specific types of IF are being made, such as α type, γ type and so on.

I claim:

1. In a process for cellular production of interferon wherein during at least a portion of the time of production, the interferon production is carried out under the influence of an interferon inducing amount of an interferon inducer, the improvement which comprises also carrying out the cellular production of interferon under the influence of an interferon production enhancement amount of sodium ethylenediaminetetraacetate.

2. In a process for enhancing the production of interferon in an interferon production system wherein during at least a portion of the time of production, the interferon production is carried out under the influence of an interferon inducing amount of an interferon inducer, the improvement, which comprises also adding to the interferon production system, an interferon production enhancement amount of sodium ethylenediaminetetraacete.

3. The process of claim 1 or claim 2 wherein the sodium ethylenediaminetetraacete is repeatedly administered.

4. The process of claim 1 or claim 2 wherein the interferon production is carried out in vivo.

5. The process of claim 1 or claim 2 wherein the interferon production is carried out in vitro and the interferon is collected.

6. The process of claim 3 wherein the interferon is collected.

* * * * *